United States Patent [19]

Zaiger

[11] Patent Number: Plant 5,463

[45] Date of Patent: May 7, 1985

[54] PEACH TREE — ZAIQUEEN CULTIVAR

[75] Inventor: Chris F. Zaiger, Modesto, Calif.

[73] Assignee: Stark Brothers Nurseries and Orchards Company, Louisiana, Mo.

[21] Appl. No.: 525,835

[22] Filed: Aug. 22, 1983

[51] Int. Cl.[3] ..... A01H 5/03

[52] U.S. Cl. ..... Plt./43

[58] Field of Search ..... Plt./43

*Primary Examiner*—Robert E. Bagwill

*Attorney, Agent, or Firm*—Burns, Doane, Swecker & Mathis

[57] ABSTRACT

A new and distinct peach variety possessing a relatively low chilling requirement is provided. The fruit of the new variety is early maturing and unlike most low chilling varieties has a higher level of red skin coloration, and excellent commercial qualities such as firmness and the ability to withstand handling and shipping. The new variety originated as an open pollinated seedling with the Ruby Gold nectarine variety (U.S. Plant Pat. No. 3,101) serving as the seed parent. Various peach varieties having low chilling requirements were growing the area and likely served as the pollen source. The new variety of the present invention is particularly suited for growing in the United States in zone 9 and the upper part of zone 10.

1 Drawing Figure

SUMMARY OF THE INVENTION

The new and distinct variety originated at my experimental orchard at Modesto, Calif. In 1972 seed which had been harvested from the Ruby Gold nectarine variety (U.S. Plant Pat. No. 3,101) was planted. Such seed was the result of open pollination and the exact source of the pollen which created the new variety accordingly is unknown. Since various peach varieties having low chilling requirements were growing in the same experimental orchard, one of these likely served as the pollen parent.

During 1976 the present variety was selected because of its distinctive characteristics and was initially designated 37G804. My continued observation of this selection has convinced me that it is a new and distinct variety.

The new variety of the present invention possesses a combination of characteristics which render it particularly suited for the commercial production of quality fruit in many mild southern regions of the United States. The low chilling requirement of the fruit is combined with excellent commercial qualities. More specifically, the new variety may be grown to advantage in the United States in zone 9 and in the upper portion of zone 10. Its fruit often ripens in early May when grown in such area.

The tree of the present variety is (a) large, vigorous and upright, (b) possesses a relatively low chilling requirement, and (c) is a productive bearer of good quality, early maturing and uniform ripening medium to large fruit having a high level of red skin coloration and a firm yellow flesh which possesses good eating and shipping qualities.

Asexual propagation at Modesto, Calif. by budding as early as 1976 and subsequent testing by me has demonstrated that the unique combination of characteristics of the new variety comes true to form and is established and transmitted through succeeding propagation. All specimens described herein were grown at Modesto, Calif.

The new variety has been named the Zaiqueen cultivar and is being marketed by Stark Brothers Nurseries and Orchards Company under the STARK and GULF QUEEN trademarks.

BRIEF DESCRIPTION OF THE PHOTOGRAPH

The accompanying photograph shows typical specimens of the fruit and foliage of the new variety in color as nearly true as it is reasonably possible to make the same in a color illustration of this character.

DETAILED DESCRIPTION OF NEW VARIETY

The following is a detailed description of the new variety where color terminology is to be accorded its ordinary dictionary significance except where otherwise indicated. The specimens described were grown at Modesto, Stanislaus County, Calif. 95351.

Representative dates of first and last pickings at Modesto, Calif. are June 2, 1980 and June 7, 1980. It should be understood, however, that when grown in a milder climate such as zone 9 of the United States the variety of the present invention will ripen in early May.

TREE

Large; vigorous; upright; medium dense; productive; regular bearing.

Trunk:

*Size.*—Medium to large.

*Texture.*—Rough and shaggy.

Branches:

*Size.*—Medium.

*Texture.*—Medium rough.

*Color.*—Light brown to brown.

*Lenticels.*—Large size and medium in number.

Leaves:

*Size.*—Large, approximately 7 to 9½ inches in length on average and approximately 1¾ to 2¼ inches in width on average.

*Texture.*—Smooth to slightly wrinkled.

*Petiole.*—Approximately ½ inch in length.

*Glands.*—Globose, 2 or 3 in number, most often 3 in number, located primarily on the base of the leaf but occasionally on the upper portion of the petiole.

*Color — upper surface.*—Dark green, 27-F-8 to 27-F-6 of the Reinhold Color Atlas by A. Kornerup and J. H. Wanscher (1961).

*Color — under surface.*—Dark green, 28-D-8 to 28-E-7 of the Reinhold Color Atlas.

*Form.*—Lanceolate, and acutely pointed.

*Margin.*—Crenate.

FLOWERS

Early, large, showy, pink in coloration, pollen is present.

FRUIT

Maturity when described: Hard ripe (i.e. shipping ripe); date — June 2 to 7, 1980.

Size: Medium to large, uniform.

*Axial diameter.*—Approximately $2\frac{1}{2}$ to $2\frac{3}{4}$ inches.

*Transverse in suture plane.*—Approximately $2\frac{1}{2}$ to $2\frac{3}{4}$ inches.

Form: Globose; slightly flattened at the stem end.

Suture: Shallow but distinct; extends from base to apex.

Ventral surface: Usually rounded and equal.

Cavity: Rounded to slightly elongated in suture plane.

Base: Retuse.

Apex: Varies from rounded to slightly pointed.

Skin: Medium thickness, medium texture, no tendency to crack, possesses scant and short down.

*Color.*—Bright yellow ground color, 4-A-8 to 5-A-8 of the Reinhold Color Atlas; and a red blush covers most of the surface, 8-B-8 to 9-B-8 of Reinhold Color Atlas.

Flesh:

*Color.*—Orange yellow, 4-A-8 to golden yellow 5-A-7 of Reinhold Color Atlas.

*Texture.*—Firm.

*Juice.*—Moderate.

*Ripens.*—Uniformly.

*Flavor.*—Mild.

*Aroma.*—Distinct.

*Fibers.*—Fine and tender.

*Eating quality.*—Good.

Stone: Clingstone. p2 *Size.*—Medium. Length. — approximately 1 3/16 inch on average. Breadth. — approximately 1 inch on average. Thickness. — approximately $\frac{3}{4}$ inch on average.

*Base.*—Straight.

*Apex.*—Acuminate.

*Sides.*—Equal to slightly unequal.

*Surface.*—Irregularly furrowed toward apex and pitted toward apex.

*Ridges.*—Rounded toward base.

*Tendency to split.*—Very slight.

*Color.*—Light brown, 8-C-4 to 8-D-4 of the Reinhold Color Atlas.

USE

Local and long distance market; dessert.

KEEPING QUALITY

Good.

SHIPPING QUALITY

Fruit ships well.

I claim:

1. A new and distinct variety of peach tree, substantially as illustrated and described, characterized by (a) a large, vigorous and upright growth habit, (b) a relatively low chilling requirement, and (c) the productive formation of good quality early maturing and uniform ripening medium to large fruit having a high level of red skin coloration and a firm yellow flesh which possesses good eating and shipping qualities.

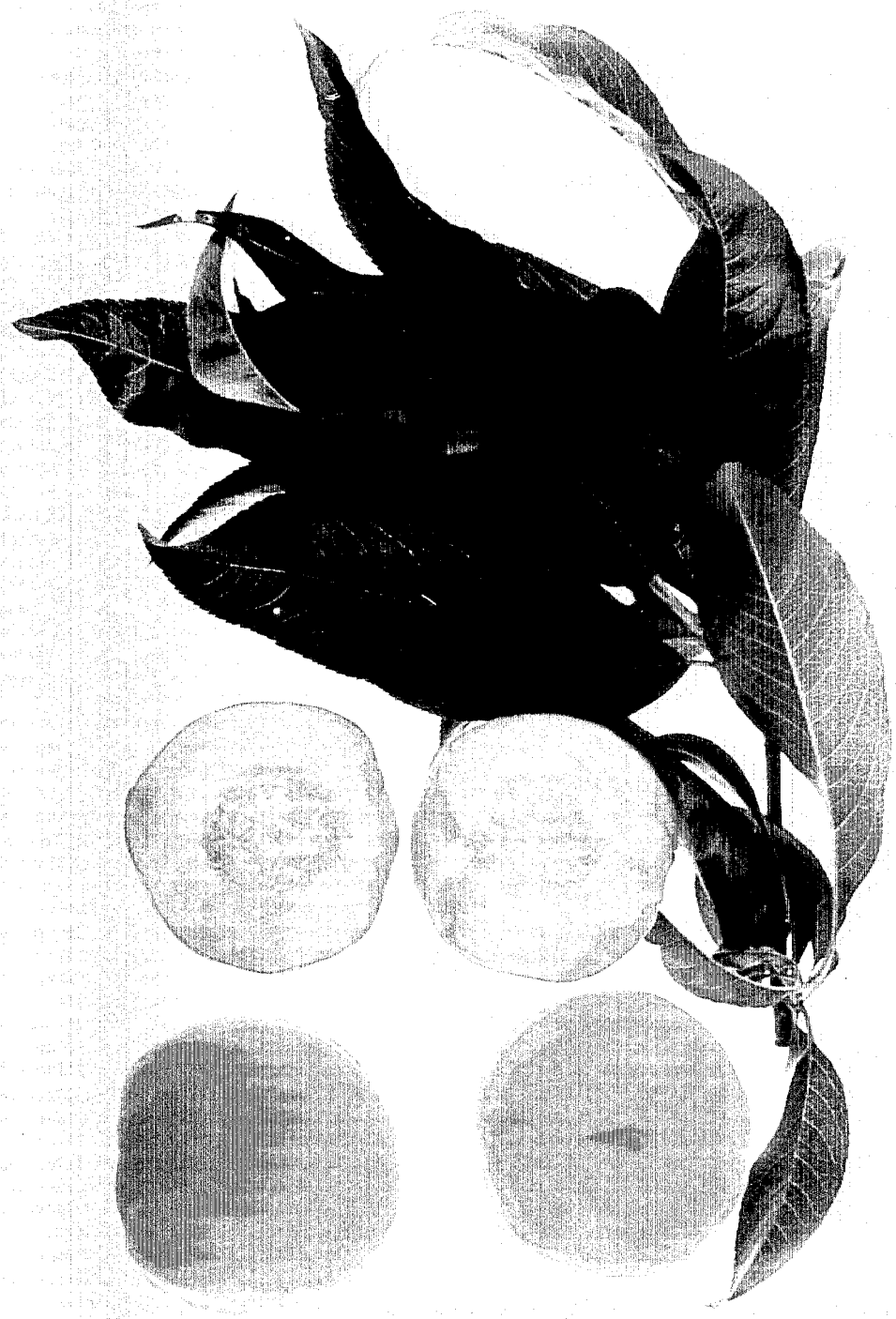

* * * * *